US00PP25675P3

(12) United States Plant Patent
Brown

(10) Patent No.: US PP25,675 P3
(45) Date of Patent: Jul. 7, 2015

(54) ***WESTRINGIA* PLANT NAMED 'WES04'**

(50) Latin Name: *Westringia fruticosa*
Varietal Denomination: WES04

(71) Applicant: Graham Brown, Cobbitty (AU)

(72) Inventor: Graham Brown, Cobbitty (AU)

( * ) Notice: Subject to any disclaimer, the term of this patent is extended or adjusted under 35 U.S.C. 154(b) by 61 days.

(21) Appl. No.: 13/986,463

(22) Filed: May 6, 2013

(65) Prior Publication Data

US 2014/0331371 P1 Nov. 6, 2014

Related U.S. Application Data

(60) Provisional application No. 61/688,192, filed on May 10, 2012.

(51) Int. Cl.
*A01H 5/00* (2006.01)

(52) U.S. Cl.
USPC ..... Plt./226
CPC ..... *A01H 5/00* (2013.01)

(58) Field of Classification Search
USPC ..... Plt./226
CPC ..... A01H 5/00
See application file for complete search history.

(56) References Cited

PUBLICATIONS

American Nurseryman, Dec. 2012.*

* cited by examiner

*Primary Examiner* — June Hwu
*Assistant Examiner* — Keith Robinson
(74) *Attorney, Agent, or Firm* — Samuel R. McCoy, Jr.

(57) ABSTRACT

'WES04' is a distinctive variety of *Westringia fruticosa* which is characterized by a combination of a rotund growth habit, compact size, gray foliage and white flowers.

1 Drawing Sheet

Latin name of the genus and species: The Latin name of the genus and species of the novel variety disclosed herein is *Westringia fruticosa.*

Variety denomination: The inventive variety of *Westringia fruticosa* disclosed herein has been given the variety denomination 'WES04'.

BACKGROUND OF THE INVENTION

The present invention relates to a new and distinct perennial variety of *Westringia fruticosa,* which has been given the variety denomination of 'WES04'. Its market class is that of an ornamental shrub. 'WES04' is intended for use in general landscaping and as a decorative plant.

Parentage: The *Westringia fruticosa* variety 'WES04' is the result of a controlled pollination breeding program from 2004 to 2009 in Cobbitty, NSW Australia. 'WES04' is a progeny of said breeding program which resulted from the cross pollination of male parent line *Westringia fruticosa* 'x2003.7.5' (unpatented) and female parent line *Westringia fruticosa* 'x2003.7.2' (unpatented). Controlled pollination of the parents occurred in September of 2004 and resulting seed from said cross was sown in March of 2005 in accord with standard greenhouse propagation practices. In October of 2005, the resulting young plants were transplanted into 10 cm nursery containers and relocated to an outdoor trial area for field observations. Progeny were further observed for desired commercial characteristics, some were subsequently eliminated and remaining candidates were transplanted into the ground for further observation. In October 2009, 'WES04' was selected for its rotund (or ball-shaped) growth habit, very compact size, gray foliage color and white flowers. The cultivar was named 'WES04'.

Asexual Reproduction: 'WES04' was first propagated asexually by division in the state of Cobbitty, New South Wales, Australia in October of 2009 and has since been asexually propagated by division through six successive generations. The distinctive characteristics of the inventive 'WES04' variety are stable from generation to generation; clones of the variety produced by asexual reproduction maintain the distinguishing characteristics of the original plant.

SUMMARY OF THE INVENTION

'WES04' is a distinctive variety of *Westringia fruticosa* which is characterized by a combination of a rotund growth habit, compact size, gray foliage and white flowers.

BRIEF DESCRIPTION OF THE FIGURES

FIG. 1 shows the original 'WES04' at four years old, in July 2011. Of note are the rotund habit, compact size and gray foliage.

BOTANICAL DESCRIPTION OF THE PLANT

The following is a detailed botanical description of a new and distinct variety of a *Westringia fruticosa* ornamental plant known as 'WES04'. Plant observations were made on the original 'WES04' plant at four years old grown in Cobbitty, New South Wales, Australia. Unless indicated otherwise, the descriptions disclosed herein are based upon observations made from mature 'WES04' plants grown from rooted cuttings from November 2010 to October 2011 in 200 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'WES04' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition. Note that generic color descriptions such as 'white' do not exist in the R.H.S. charts and the corresponding R.H.S. colors are quoted.

Technical Description of the Variety

Plant description:

*Plant habit*.—Shrub; upright, rounded and dense.

*Height*.—45 cm at maturity.

*Width*.—45 cm at maturity.

*Bloom period*.—Spring.

*Hardiness*.—USDA Zone 9 to 11.

*Propagation*.—Propagation is accomplished using semi-hard wood cuttings. Roots well without rooting compound or hormone.

*Time to develop roots*.—Approximately 3 weeks.

*Crop time*.—From approximately three to four months are needed to produce a well rooted 1-gallon nursery pot, starting from a rooted cutting. Crop time varies with location and production practices.

Roots: The roots of 'WES04' are colored white and fleshy and thick, similar to other *Westringia fruticosa*.

Stem:

*Stem strength*.—Medium.

*Attitude*.—Acutely branched and upright.

*Shape*.—Cylindrical yet angular.

*Stem color*.—Young stem is closest to green 138C.

*Stem dimensions*.—Mature stem, 10 nodes below the actively growing tip, are approximately 12 mm in length with a diameter of 2.5 mm.

*Stem surface*.—Corky and pruinose.

*Basal stem color*.—Mature stems closest to yellow green 146C.

*Internode length*.—12 mm on average.

Foliage:

*Type*.—Evergreen.

*Shape*.—Ovate.

*Division*.—Simple.

*Apex*.—Acute.

*Base*.—Cuneate.

*Venation*.—Reticulate but not obvious.

*Vein color* (*adaxial surfaces*).—147A.

*Vein color* (*abaxial surfaces*).—N155A.

*Margins*.—Entire.

*Arrangement*.—Whorled.

*Attachment*.—Petiolate.

*Texture*.—Leathery.

*Surfaces* (*adaxial surface*).—Moderately pubescent.

*Surfaces* (*abaxial surface*).—Heavily pubescent.

*Mature leaf dimensions*.—Average length, 13 mm; width is 7 mm.

*Leaf color* (*adaxial surface*).—147A.

*Leaf color* (*abaxial surface*).—N155A.

*Petiole*.—Approximately 2 mm in length; width minute.

*Stipules*.—Absent.

Inflorescence: None; flowers are sessile.

Bud: Obovoid in shape and rounded at the apex. Approximately 6 mm long and 3 mm wide prior to dehiscence. Color is white 155C.

Flower:

*General*.—Flowers are sessile, simple and persist for approximately 5 days. Self cleaning. Non fragrant.

*Flowers*.—Small; Sympetalous, irregular with sepals numbering five; bilabiate with upper lip erect and two-lobed and lower lip spreading and three-lobed; lobes obovate with apex retuse and undulating; width across the corolla measuring on average 12 mm and a length, from base of perianth to tip of sepal lobe measures 13 mm (average); color is white 155C. Spots, or "eyes", present; color closest to 31 A.

*Calyx*.—Synsepalous with five calyx lobes; green (RHS 138C). The length of the sepal is 6 mm.

Reproductive organs:

*Stamens*.—4 and 2 staminodes.

*Stamen color*.—White (no R.H.S. match).

*Stamen dimensions*.—About 3 mm in length and approximately 0.5 mm wide.

*Attachment*.—Adnate.

*Anther dimensions*.—Minute; less than 1 mm.

*Anther color*.—15D.

*Pollen*.—Absent.

*Pistil*.—One.

*Pistil dimensions*.—About 7 mm in length and approximately 0.5 mm wide.

*Pistil color*.—White (no R.H.S. match).

*Ovary position*.—Superior.

Fruit and seed: Non-fleshy schizocarp with four mericarps, in four distinct segments. Texture is rough or wrinkled; color appears as a combination of greyed-yellow (RHS 160A) and greyed-orange (RHS 165C); dimensions are approximately 4 mm long and 5 mm across.

Environmental tolerances:

*Cold and heat tolerance*.—The winter hardiness of 'WES04' is at least to USDA Zone 9a and evaluation of winter hardiness is ongoing. 'WES04' has heat tolerance typical of *Westringia fruticosa*.

*Drought tolerance*.—'WES04' has good drought tolerance typical of *Westringia fruticosa* once established.

*Pest resistance*.—No known insect or disease pests.

*Cultural conditions*.—*Westringia* is commonly known to perform well in sandy soils, but also tolerates heavy, clay-type soils well. 'WES04' can also be grown in a relatively wide pH range and is also tolerant of above-normal salt concentration in the soil environment and is also tolerant of aerosol salt exposure; e.g. coastal exposure to salt laden winds.

Comparison of WES04 with Other Varieties of Hybrid *Westringia*

For the purpose of this comparison, the expression of plant characteristics such as "short" and "tall" are employed in accord with the DUS Test Guidelines established under the 1991 Act of the International Union for the Protection of New Varieties of Plants (UPOV) Convention.

'WES04' has a rotund growth habit and a short plant height whereas the seed parent, 'x2003.7.2' (unpatented) has a mounding habit and medium plant height. The pollen parent 'x2003.7.5', by comparison, has an upright growth habit and tall plant height.

'WES04' can be compared to several similar varieties of common knowledge: *Westringia fruticosa* 'Milky Way' (unpatented), *Westringia fruticosa* 'Jervis Gem' (unpatented), *Westringia fruticosa* 'Zena' (unpatented) and *Westringia* sp. 'Seaform White'. However, 'WES04' is a significantly smaller plant with mature dimensions of approximately 45 cm tall and 45 cm wide whereas all three of the said comparators are approximately 100 cm tall and 100 cm wide, at maturity. The flowers of 'WES04' are white (no corresponding R.H.S. color) whereas the flowers of 'Jervis Gem' are purple (76B). 'WES04' is observed to have short internodes of approximately 12 mm in length whereas both 'Zena' and 'Seafoam White' have internodes of medium length. 'WES04' is similar to 'Milky Way' in height and foliage color however specific, distinguishing differences are of note. 'WES04' is compact and rotund with overall plant size dimensions approximating to 45 cm tall and 45 cm wide whereas 'Milky Way' is approximately 50 cm tall but spreads more to a width of approximately 85 cm. Also, 'WES04' has a small leaf and medium flower diameter (across the corolla) whereas 'Milky Way' has a very small leaf and small flower diameter.

That which is claimed is:

1. A new and distinct variety of *Westringia fruticosa* plant named 'WES04', substantially as described and illustrated herein.

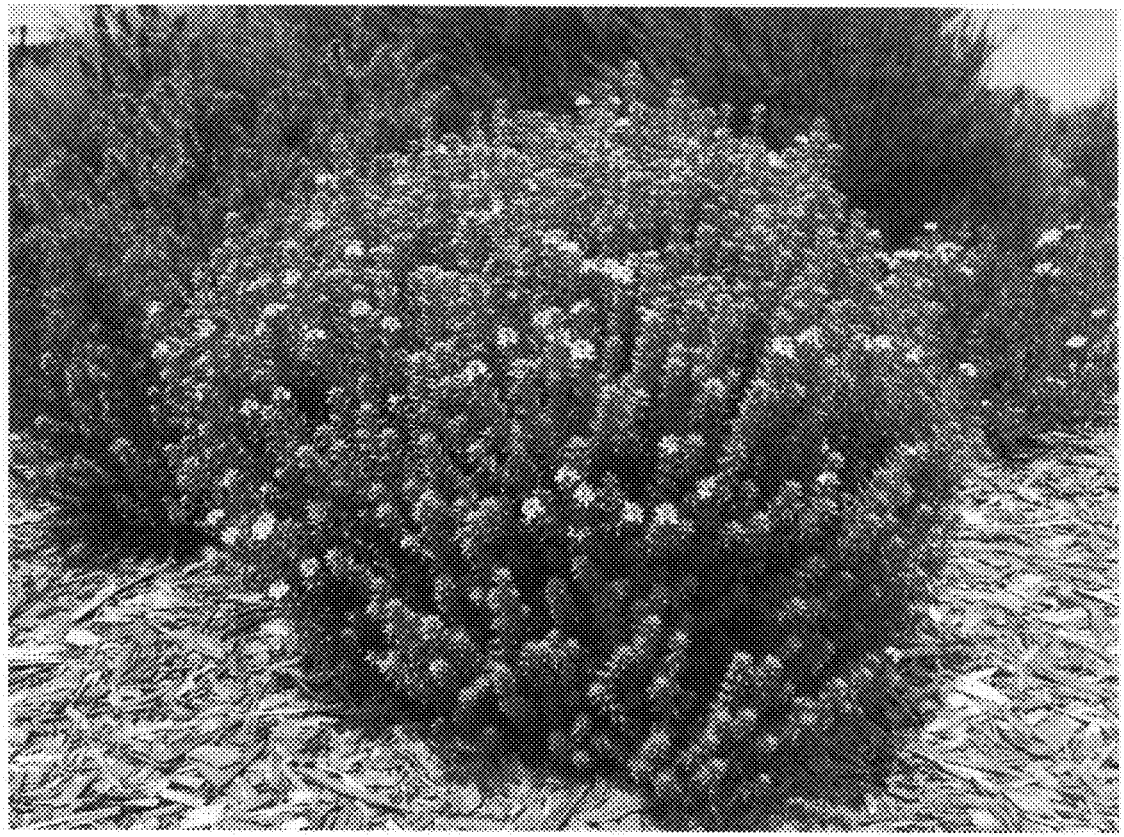

* * * * *